Figure 1:
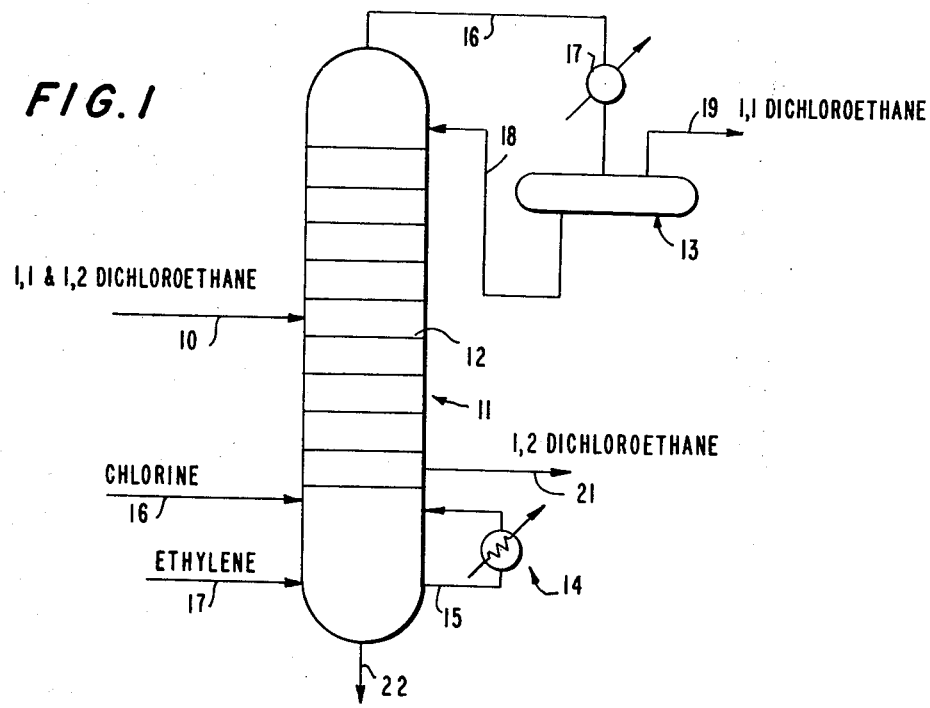

United States Patent [19]

Tsao

[11] 3,985,816

[45] Oct. 12, 1976

[54] SEPARATION OF 1,1-DICHLOROETHANE FROM 1,2-DICHLOROETHANE
[75] Inventor: Utah Tsao, Jersey City, N.J.
[73] Assignee: The Lummus Company, Bloomfield, N.J.
[22] Filed: Apr. 4, 1975
[21] Appl. No.: 565,204

Related U.S. Application Data
[62] Division of Ser. No. 498,083, Aug. 16, 1974, Pat. No. 3,917,727.

[52] U.S. Cl. .............................. 260/652 P; 260/660; 260/656 R
[51] Int. Cl.² .................. C07C 17/38; C07C 17/02
[58] Field of Search ............ 260/660, 652 P, 656 R

[56] References Cited
UNITED STATES PATENTS
1,231,123   6/1917   Brooks et al. ...................... 260/660
3,846,253   11/1974  Obrecht ........................... 260/652 P FOREIGN PATENTS OR APPLICATIONS
689,991   7/1964   Canada .............................. 260/660

Primary Examiner—D. Horwitz
Attorney, Agent, or Firm—Marn & Jangarathis

[57] ABSTRACT

In the fractionation of 1,1-dichloroethane and 1,2-dichloroethane, at least a portion of the reboil heat requirements for the fractionation is provided by chlorinating ethylene in the fractional distillation tower. The fractionation is particularly applicable to the production of vinyl chloride by the use of molten salts wherein ethylene is present as a by-product.

4 Claims, 4 Drawing Figures

SEPARATION OF 1,1-DICHLOROETHANE FROM 1,2-DICHLOROETHANE

This is a division of application Ser. No. 498,083, filed Aug. 16, 1974 and now U.S. Pat. No. 3,917,727.

The present invention is directed to the fractionation of 1,1-dichloroethane and 1,2-dichloroethane. This invention further relates to the fractionation of 1,1-dichloroethane and 1,2-dichloroethane in an overall process for producing vinyl chloride.

In many processes, there is a need to fractionate 1,1-dichloroethane and 1,2-dichloroethane. Although such a fractionation may be readily effected, the heat requirements thereof are high.

Thus, for example, in an overall process for producing vinyl chloride from ethane, as described in application Ser. No. 153,374, filed June 15, 1971 and now U.S. Pat. No. 3,937,744 and application Ser. No. 157,496 filed June 28, 1971 and now U.S. Pat. No. 3,879,482, 1,1-dichloroethane and 1,2-dichloroethane, may be produced during the chlorination, and in such a process, it is sometimes desirable to recover 1,2-dichloroethane, as a separate reaction product, or to separately dehydrochlorinate 1,1-dichloroethane and 1,2-dichloroethane to vinyl chloride. Accordingly, there is a need to reduce the utilities requirements for such a fractionation.

An object of the present invention is to provide for improved fractionation of 1,1-dichloroethane and 1,2-dichloroethane.

Another object of the present invention is to provide for the fractionation of 1,1-dichloroethane and 1,2-dichloroethane with reduced utilities requirements.

A further object of the present invention is to provide for improved fractionation of 1,1-dichloroethane and 1,2-dichloroethane in a process for producing vinyl chloride.

Figure 2:
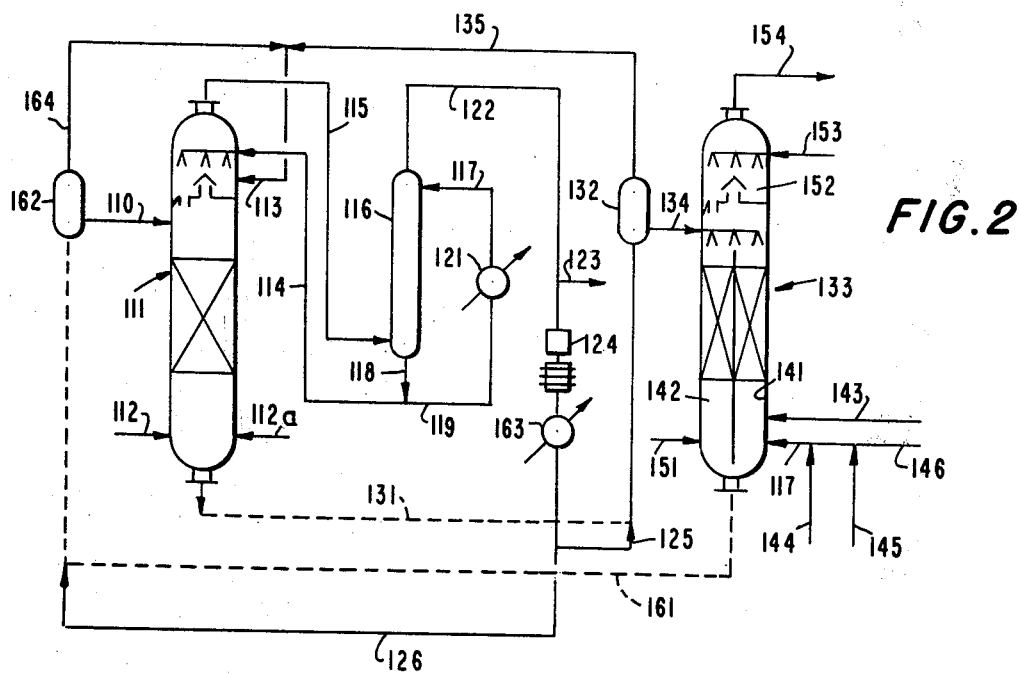
Figure 3:
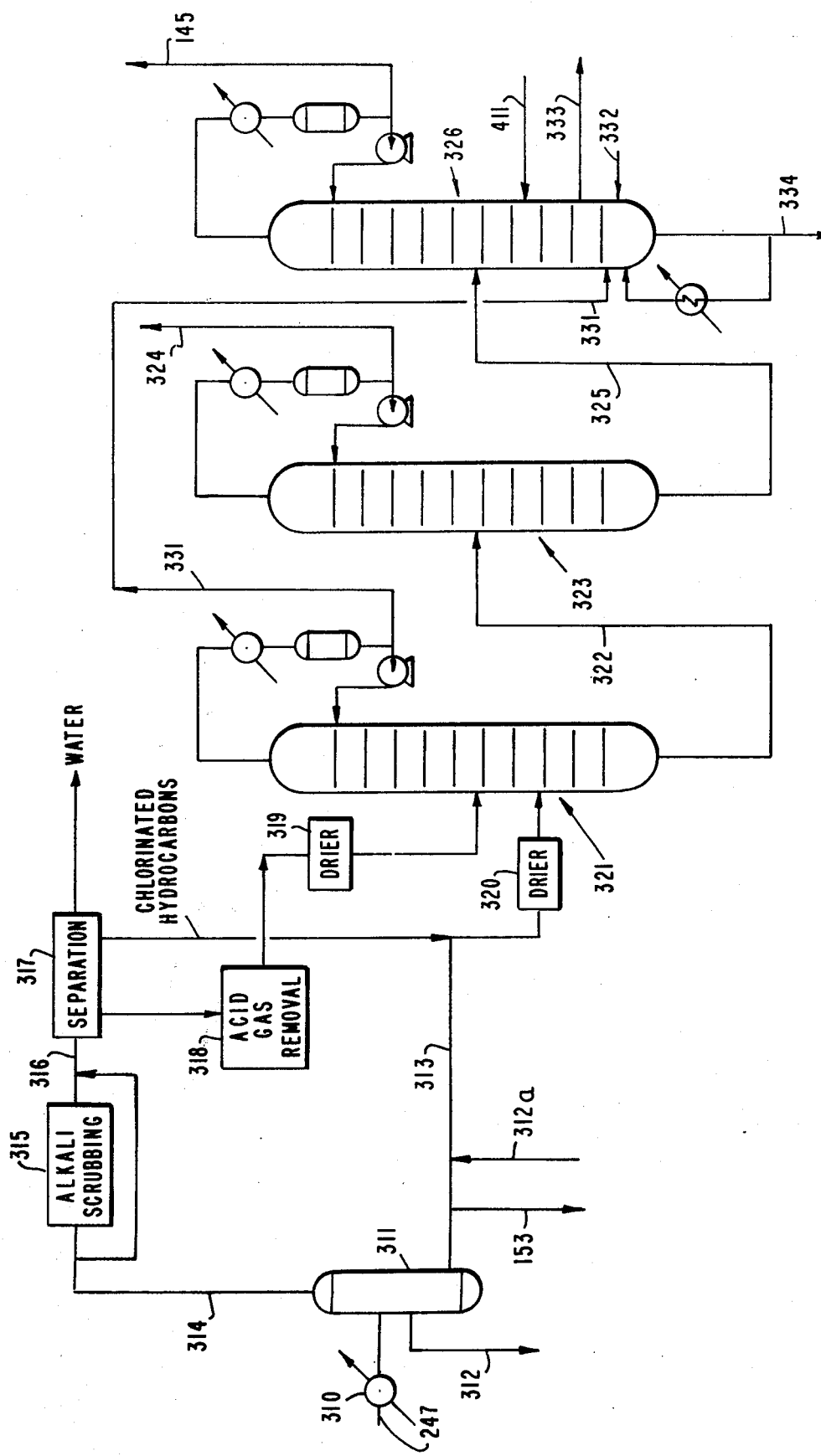
Figure 4:
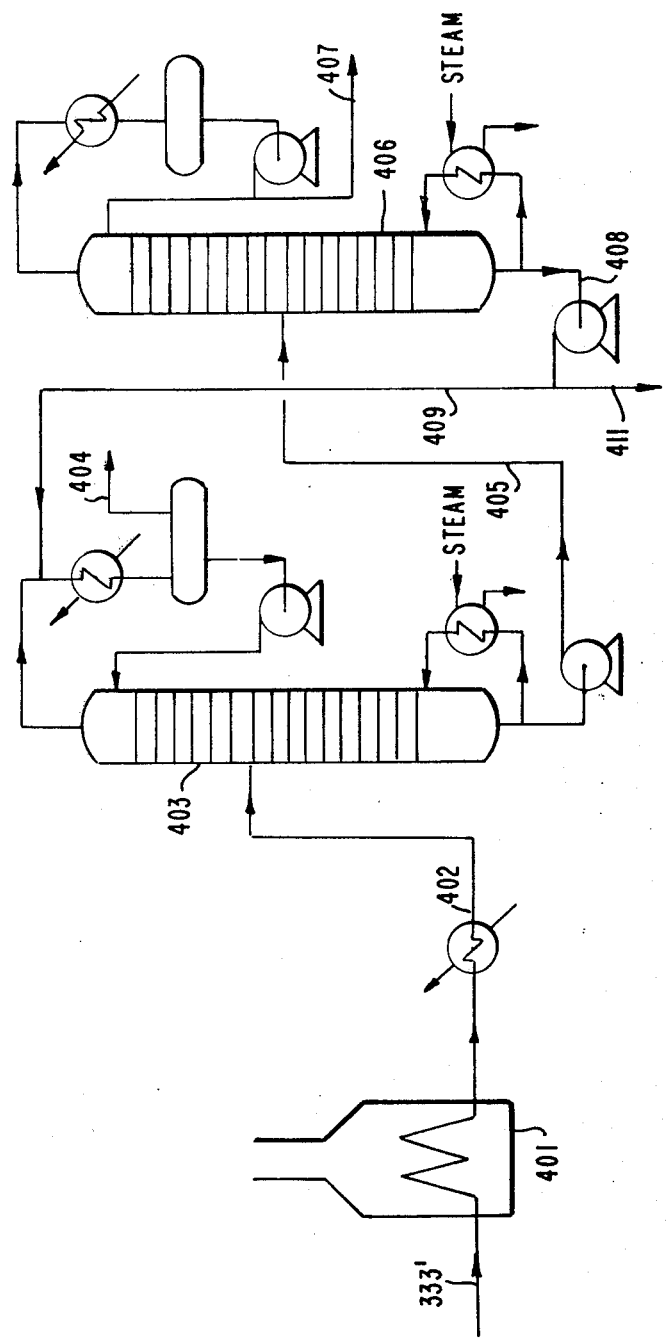

These and other objects of the invention should be more readily apparent from reading the following description of the invention with reference to the accompanying drawings wherein:

FIG. 1 is a simplified schematic flow diagram of an embodiment of the present invention;

FIG. 2 is a simplified schematic flow diagram of the reaction portion of an overall process for producing vinyl chloride which incorporates the teachings of the present invention; and FIG. 3 is a simplified schematic flow diagram of a portion of the separation and recovery section of the overall process for producing vinyl chloride; and FIG. 4 is a simplified schematic flow diagram of a portion of a modified embodiment of an overall process for producing vinyl chloride incorporating the teachings of the present invention.

The objects of the present invention are broadly accomplished in one aspect, by fractionating 1,1-dichloroethane and 1,2-dichloroethane in a fractionating zone while simultaneously chlorinating ethylene therein the aforesaid chlorination of ethylene being exothermic, whereby at least a portion of the heat requirements for the aforesaid fractionation are provided by the exothermic chlorination.

More particularly, a feed containing 1,1-dichloroethane and 1,2-dichloroethane is fractionated at temperatures and pressures whereby 1,1-dichloroethane is recovered from the fractional distillation column as a first stream and 1,2-dichloroethane is recovered from the fractional distillation column as a second stream with ethylene and chlorine also being introduced into the fractional distillation column, whereby at the fractionation conditions, the exothermic chlorination of the ethylene, to produce primarily 1,2-dichloroethane, provides at least a portion of the heat requirements for the fractional distillation. The 1,2-dichloroethane produced during the chlorination is recovered with the 1,2-dichloroethane introduced as feed to the fractional distillation zone. The fractional distillation column is operated at any temperatures and pressures which are suitable for effecting both the desired fractionation and chlorination of ethylene.

In general, the fractional distillation column is operated at an overhead temperature from about 170° F to about 310° F, a bottom temperature from about 230° F to about 360° F and a column pressure from about 2 atm to about 10 atm (absolute). The chlorination of ethylene is preferably effected in the liquid phase at the bottom of the column, with 1,2-dichloroethane functioning as the reaction medium. As generally known in the art, the liquid phase reaction of chlorine and ethylene is preferably effected in the presence of a catalyst and any catalyst which is suitable for such a reaction is suitable for the purposes of the present invention. As representative examples of such catalysts, there may be mentioned metal chlorides, such as copper chloride, iron chloride, antimony chloride and the like, but it is to be understood that the present invention is not limited to a particular catalyst.

The ethylene and chlorine added to the fractional distillation zone are preferably added in about stoichiometric proportions in order to insure essentially complete reaction thereof. It is to be understood, however, that amounts other than stoichiometric proportions may be used within the spirit and scope of the present invention.

The feed to the fractionation zone may include components other than 1,1- and 1,2-dichloroethane and ethylene and chlorine, as hereinafter described, and, accordingly, the teachings of the present invention are also applicable to feeds including such other components.

The present invention will be further described with respect to an embodiment thereof illustrated in the accompanying drawing, but it is to be understood that the scope of the present invention is not to be limited by the embodiment particularly described.

Referring now to FIG. 1, a feed containing 1,1- and 1,2-dichloroethane is introduced through line 10 into an intermediate portion of a fractional distillation column, generally indicated as 11, of a type known in the art. The fractional distillation column includes suitable means for increasing vapor liquid contact, such as a plurality of trays 12. The fractionator 11 is operated at temperatures and a pressure, as hereinabove described, for fractionating 1,1-dichloroethane and 1,2-dichloroethane. The fractionator is provided with a suitable reflux section, generally designated as 13, and a suitable reboil section, generally designated as 14.

The bottom of the column 11 forms a reaction section 15 which includes a liquid comprised essentially of 1,2-dichloroethane, which also includes a suitable chlorination catalyst, such as ferric chloride. Fresh feed chlorine in line 16 and fresh feed ethylene in line 17 is introduced into the liquid containing reaction section 15 of the column 11 for chlorinaton of the ethylene to 1,2-dichloroethane.

The chlorination of ethylene is exothermic and the exothermic heat of chlorination provides at least a portion of the heat required for effecting reboil of the liquid maintained in the bottom of the column 11. The remaining portion of the heat requirements, if any, is provided by the reboil section 14.

The 1,1-dichloroethane fractionated from the feed introduced into column 11 through line 10 is withdrawn, as overhead, through line 16 and passed through a condenser 17 to condense a portion thereof. The condensed portion is returned, as reflux, to column 11 through line 18, and 1,1-dichloroethane is recovered, as a net overhead product, through line 19.

1,2-dichloroethane, both fractionated from the feed introduced into column 11 through line 10, and that produced by chlorination of ethylene, is recovered as a sidestream through line 21. The sidestream could include some more fully chlorinated by-products. The fractionator 11 is also provided with an outlet 22 for recovering more fully chlorinated hydrocarbons, such as trichloroethane, therefrom. It is to be understood that the 1,2-dichloroethane could be recovered as bottoms instead of as a sidestream.

The teachings of the present invention with respect to the improved fractionation of a mixture of 1,1-dichloroethane and 1,2-dichloroethane are particularly applicable to a process for producing vinyl chloride. In such a process ethane is chlorinated to produce a reaction effluent which includes vinyl chloride, 1,2-dichloroethane, 1,1-dichloroethane and ethylene. The reaction effluent is passed to a separation and recovery zone wherein vinyl chloride, ethylene and a mixture including 1,1-dichloroethane and 1,2-dichloroethane are separated as separate streams. The mixture of 1,1-dichloroethane and 1,2-dichloroethane is then fractionated in accordance with the teachings of the present invention, with the ethylene which is recovered from the reaction effluent being used as feed to the fractionation zone for the exothermic chlorination thereof to 1,2-dichloroethane. The 1,2-dichloroethane separated in the fractionation zone may be recovered as a reaction product or dehydrochlorinated to vinyl chloride.

The teachings of the present invention are preferably applied to a process for producing vinyl chloride by the use of molten salts, but it is to be understood that the invention is not limited to such an application.

More particularly, ethane and clorine and/or hydrogen chloride are contacted in a chlorination zone with a molten mixture including a multivalent metal chloride in both its higher and lower valence state and the oxychloride of the metal, to produce a chlorination reaction effluent which includes vinyl chloride, 1,2-dichloroethane, 1,1-dichloroethane, ethyl chloride, ethylene and unreacted ethane. The reaction effluent is introduced into a separation and recovery section in which unreacted ethane and ethylene are recovered as a separate stream, and vinyl chloride is recovered as product. The remaining reaction effluent, including 1,1-dichloroethane, 1,2-dichloroethane and ethyl chloride, is introduced into a fractional distillation zone designed and operated to recover 1,1-dichloroethane and lighter components, as overhead. The recovered ethane-ethylene stream and chlorine are introduced into the aforesaid fractional distillation zone, and the ethylene is exothermically chlorinated therein to 1,2-dichloroethane, with the exothermic chlorination providing at least a portion of the heat requirements for the fractional distillation. An overhead stream comprised of 1,1-dichloroethane, ethyl chloride, ethane and any unconverted ethylene are recycled to the chlorination zone for ultimate conversion to vinyl chloride.

The recovered 1,2-dichloroethane is recovered as product or dehydrochlorinated to vinyl chloride.

The melt contains a chloride of a multivalent metal; i.e., a metal having more than one positive valence state, such as, manganese, iron, copper, cobalt, and chromium, preferably copper. In the case of higher melting multivalent metal chlorides, such as copper chlorides, a metal salt melting point depressant which is non-volatile and resistant to oxygen at the process conditions, such as a chloride of a univalent metal i.e., a metal having only one positive valence state, is added to the multivalent metal chloride to form a molten salt mixture having a reduced melting point. The univalent metal chlorides, are preferably alkali metal chlorides, such as potassium and lithium chloride in particular, but it is to be understood that other metal chlorides and mixtures thereof, such as the heavy metal chlorides (heavier than copper) of Groups I, II, III and IV of the Periodic Table; e.g., zinc, silver, and thallium chloride, may also be employed. The metal chloride melting point depressant is added in an amount sufficient to maintain the salt mixture as a melt at the reaction temperatures and is generally added in an amount sufficient to adjust the melting point of the molten salt mixture to a temperature of below about 500° F. In the case of a salt mixture of copper chloride and potassium chloride, the composition of the melt ranges from about 20% to about 40%, preferably about 30%, by weight, potassium chloride, with the remainder being copper chlorides. It is to be understood, however, that in some cases the catalyst melt may have a melting point higher than 500° F, provided the catalyst remains in the form of the melt throughout the processing steps. It is further to be understood that the melt may contain a mixture of multivalent metal chlorides or other reaction promoters. It is also to be understood that in some cases, the metal chloride may be maintained as a melt without the addition of a melting point depressant.

The reaction sequence for chlorinating ethane to vinyl chloride, using copper chloride as a representative multivalent metal chloride, is believed to be best represented by the following equations:

1. $C_2H_6 + Cl_2 \rightarrow C_2H_5Cl + HCl$

2. $C_2H_5Cl + Cl_2 \rightarrow C_2H_4Cl_2 + HCl$

3. $C_2H_5Cl \rightarrow C_2H_4 + HCl$

4. $C_2H_4 + Cl_2 \rightarrow C_2H_4Cl_2$

5. $C_2H_4Cl_2 \rightarrow C_2H_3Cl + HCl$

6. $CuO \cdot CuCl_2 + 2HCl \rightarrow 2CuCl_2 + H_2O$

7. $2CuCl_2 \rightarrow 2CuCl + Cl_2$

8. $2CuCl + Cl_2 \rightarrow 2CuCl_2$

Thus, the various reactions which are believed to be effected during the chlorination provide for chlorination of ethane to vinyl cloride, and effective utilization of the reaction intermediates, ethyl chloride, ethylene and hydrogen chloride by ultimate conversion thereof to vinyl chloride.

The oxychloride of the multivalent metal which is present in the melt may be generated by previously contacting the melt with molecular oxygen, with the reaction being represented by the following equation:

9. $2CuCl + \frac{1}{2}O_2 \rightarrow CuO \cdot CuCl_2$

The generated hydrogen chloride reacts with the copper oxychloride of the melt, as represented by the following equation:

10. $CuO \cdot CuCl_2 + 2HCl \rightarrow 2CuCl_2 + H_2O$

The overall reaction for producing vinyl chloride from ethane and chlorine and/or hydrogen chloride is represented by the following overall equations:

11. $C_2H_6 + \frac{1}{2}Cl_2 + \frac{3}{4}O_2 \rightarrow C_2H_3Cl + 3/2H_2O$
12. $C_2H_6 + HCl + O_2 \rightarrow C_2H_3Cl + 2H_2O$ Accordingly, the present invention provides a process for producing vinyl chloride from ethane with essentially all of the ethane and chlorine and/or hydrogen chloride, added as fresh feed, being ultimately converted to vinyl chloride.

The chlorination reaction for producing vinyl chloride from ethane may be effected at temperatures from about 700° F to about 1200° F and at pressures from about 1 to about 20 atmospheres. The chlorination reaction is preferably effected at temperatures from about 750° F to about 1000° F and more preferably from about 800° F to about 900° F in that such temperature conditions, in combination with the other processing conditions, have been found to provide improved yields of vinyl chloride. The contacting of the feed and melt is generally effected in a countercurrent fashion, preferably with the feed as a continuous vapor phase, at residence times from about 1 to about 60 seconds, although longer residence times may be employed.

The molten mixture introduced into the chlorination zone generally contains from about 0.5% to about 5.5% preferably from about 1% to about 3%, all by weight, of the oxychloride, preferably copper oxychloride, and at least about 16% of the higher valent metal chloride, preferably from about 18% to about 50% and more preferably from about 20% to about 35%, all by weight, of the higher valent metal chloride, with the higher valent metal chloride preferably being cupric chloride. The remainder of the melt is comprised of the lower valent metal chloride and the melting point depressant, preferably potassium chloride. In the case of a molten mixture of cuprous chloride, cupric chloride, potassium chloride and copper oxychloride, the copper oxychloride and cupric chloride are present in the amounts hereinabove described, the potassium chloride in an amount from about 20% to about 40%, by weight, with the remainder being cuprous chloride, based on the four components. As a result of the various reactions which are effected during the process, the cupric chloride content of the melt does not significantly vary through the various reaction zones. The molten salt is circulated at a rate to provide a molten salt to feed weight ratio (based on total feed; i.e., including recycle to the chlorination zone) from about 25:1 to about 200:1, and preferably from about 50:1 to about 25:1.

In ethane, as fresh feed, the total chlorine employed in the process generally approximates stoichiometric proportions in order to eliminate the necessity for chlorine recovery and recycle, generally in amounts to provide a chlorine to ethane fresh feed weight ratio from about 1.0:1 to about 1.2:1. In accordance with the present invention, a portion of the total chlorine is introduced into the 1,1- 1,2-dichloroethane fractionator to effect chlorination of ethylene therein. The portion of total chlorine introduced into the fractionator is preferably in an amount which is about stoichiometric to the amount of ethylene introduced in the feed to the fractionator. The ethyl chloride recycled to the chlorination zone is in a amount to provide an ethyl chloride to ethane fresh feed weight ratio from about 0.3:1 to about 14:1, preferably from about 1:1 to about 8:1. In the case where hydrogen chloride is used as the chlorinating agent, hydrogen chloride is used in less than stoichiometric proportions, with the remainder of the stoichiometric requirements being provided by the introduction of chlorine into the dichloroethane fractionator. The amount of chlorine introduced into the fractionator corresponds to that about stoichiometrically required for reaction with the ethylene.

The 1,2-dichloroethane generated during the chlorination is either recovered as product or recovered and dehydrochlorinated to vinyl chloride. The reaction product from the chlorination reactor, as hereinabove noted, also includes 1,1-dichloroethane and ethylene and, accordingly, the teachings of the invention may be utilized to effect separation of 1,1-dichloroethane and 1,2-dichloroethane by chlorination of ethylene recovered from the chlorination effluent. The conditions for effecting such fractionation are as hereinabove noted, and at such conditions, ethylene is exothermically chlorinated to 1,2-dichloroethane to provide at least a portion of the heat requirements for the fractionation of 1,1- and 1,2-dichloroethane. The 1,1-dichloroethane recovered during the fractionation is recycled to the chlorination reaction zone for dehydrochlorination to vinyl chloride (Equation 5).

If the 1,2-dichloroethane is to be converted to vinyl chloride, such dehydrochlorination may be effected as known in the art, with the dehydrochlorination generally being effected at temperatures from about 700° F to about 1200° F. The dehydrochlorination may be effected thermally in a suitable furnace as known in the art, or catalytically with any of the wide variety of known solid dehydrochlorination catalysts (in general even in thermal processes a minor portion of chlorine is added to the feed as a free radical generator). Alternatively, the dichloroethane may be dehydrochlorinated in a separate reaction zone using a molten salt mixture as described in the aforementioned application Ser. No. 153,374. The hydrogen chloride released during the dehydrochlorination is recovered from the effluent, and employed for the chlorination step. In the case where a molten mixture which includes oxychloride is employed for the dehydrochlorination, the effluent includes only equilibrium amounts of hydrogen chloride. In view of the fact that the details of the dehydrochlorination reaction for dehydrochlorinating 1,2-dichloroethane forms no part of the present invention, and that the dehydrochlorination of 1,2-dichloroethane is well known in the art, no further discussion of this processing step is deemed necessary for a full understanding of the present invention.

The oxychloride of the melt, as hereinabove noted, is preferably provided by contacting a molten mixture including the multivalent metal chloride in both its higher and lower valence state with a molecular oxygen-containing gas, such as air, prior to introducing the molten mixture into the chlorination reaction zone. The contacting of the melt and oxygen may be effected at a temperature from about 600° F to about 900° F, and preferably at a temperature from about 750° F to about 870° F. The contacting of the oxygen and melt is effected at a rate to provide a molten mixture having a copper oxychloride content in the amounts hereinabove described. It is to be understood that minor amounts of chlorine and/or hydrogen chloride could also be introduced during oxidation of the melt, with such chlorine and/or hydrogen chloride reacting with the melt as defined in Equations (8) and (10).

The molten salt mixture, in addition to functioning as a reactant and/or catalyst, is a temperature regulator. Thus, the circulating melt has a high heat absorption capacity, thereby preventing runaway reaction during the exothermic chlorination and oxygen contacting steps; the temperature fluctuation between the oxidation and chlorination zones is generally no greater than about 130° F, and in most cases, the temperature fluctuation is from about 15° F to 50° F. In general, the overall chlorination and oxidation reaction provides a net exotherm and some cooling of the melt is required. The temperature of the melt may be regulated by adjusting the temperatures of the various feed streams whereby the absorbed heat of reaction is employed to heat the streams to reaction temperature. Alternatively, the temperature of the lift gas employed for transporting the melt can be regulated.

The invention will now be further described with reference to further embodiments thereof illustrated in the accompanying drawings. It is to be understood however, that the scope of the invention is not to be limited thereby. It is further to be understood that the molten copper chloride salts are highly corrosive and, accordingly, the processing equipment must be suitably protected; e.g., the reactors may be lined with ceramic. Similarly, if pumps are used for transporting the molten salts they must also be protected. The molten salts, however, are preferably transferred between the reactors by the use of gas lifts, as known in the art.

Referring now to FIG. 2, a molten chloride salt, such as a mixture of potassium chloride, cuprous chloride and cupric chloride in line 110 is introduced into the top of the reaction portion of an oxidation vessel 111 maintained, as hereinabove described, at temperatures and pressures suitable for oxidizing the molten salt. A compressed oxygen-containing gas, such as air, in line 112 is introduced into the bottom of vessel 111 and is passed in countercurrent contact to the descending molten salt, resulting in oxidation of the salt to produce copper oxychloride with the concurrent evolution of heat. In addition, a combustion effluent resulting from the combustion of heavier chlorinated by-products, such as tri- and tetrachloroethanes and ethylenes and including hydrogen chloride and/or chlorine may be introduced into vessel 111 through line 112a, as described in U.S. application Ser. No. 95,030 filed Dec. 4, 1970.

An effluent gas, comprised essentially of the nitrogen introduced with the air, (the effluent could also include combustion products as described in U.S. application Ser. No. 95,030 if a combustion effluent is introduced through line 112a) rises into the top of the vessel 111 wherein the effluent gas is combined with lift gas, as hereinafter described, introduced through line 113. The effluent gas is directly contacted in the top of vessel 111 with a spray of quench liquid, in particular aqueous hydrogen chloride introduced through line 114 to cool the effluent gas and thereby eliminate any vaporized and entrained salts therefrom. The effluent gas, now containing vaporized quench liquid, is withdrawn from vessel 111 through line 115 and introduced into a direct contact quench tower 116, of a type known in the art wherein the effluent gas is cooled by direct contact with a suitable quench liquid, in particular aqueous hydrogen chloride, introduced through line 17 to thereby remove vaporized quench liquid from the effluent gas.

The quench liquid is withdrawn from the bottom of tower 116 through line 118 and a first portion passed through line 114 for quenching the effluent gas in vessel 111. A second portion of the quench liquid is passed through line 119, containing a cooler 121, for introduction into the quench tower 116 through line 117.

An effluent gas, comprised essentially of nitrogen, is withdrawn from quench tower 116 through line 122 and a portion thereof purged through line 123. The remaining portion of the nitrogen effluent gas is compressed in compressor 124 and the temperature thereof regulated in heat exchanger 163 prior to passage through lines 125 and 126 for use as a lift gas for transporting molten salt, as hereinafter described.

The molten salt, now containing copper oxychloride, is withdrawn from the bottom of vessel 111 through line 131 and lifted by the lift gas in line 125 into a separation vessel 132 positioned adjacent the top of the reaction portion of a reaction vessel 133. In separator 132, the molten salt is separated from the lift gas, with the separated lift gas being withdrawn through line 135 and combined with lift gas from the oxidation reactor for introduction into the quenching portion of vessel 111 through line 113.

The reaction vessel 133 is divided into two separate reaction sections, 141 and 142 with reaction section 141 functioning as a chlorination reaction zone and section 142 as a dehydrochlorination reaction zone. The molten salt, containing cuprous chloride, cupric chlorine copper oxychloride and the potassium chloride melting point depressant, from separator 132, in line 134, is introduced into both reaction sections 141 and 142.

Fresh feed chloride and/or hydrogen chloride is introduced into the bottom of section 141 through 143 and fresh feed ethane in line 144 is combined with a recycle comprised primarily of ethyl chloride ethane and 1,1-dichloroethane, in line 145, for introduction into the bottom of section 141 through line 147.

The reaction section 141 is operated at the temperatures and pressures, hereinabove described, to produce an effluent which contains, as combined reaction product, vinyl chloride and 1,2-dichloroethane. The effluent also includes, ethyl chloride, 1,1-dichlorethane, ethane, ethylene, water vapor, some hydrogen chloride and heavier chlorinated hydrocarbons.

1,2-dichloroethane in line 151 is introduced into the bottom of reaction section 142 and countercurrently contacts the descending molten salt. As a result of such contact, the 1,2-dichloroethane is dehydrochlorinated to vinyl chloride. The hydrogen chloride generated during the dehydrochlorination, as hereinabove noted, reacts with the oxychloride present in the melt.

The reaction effluent from chlorination section 141 is combined with the reaction effluent from dehydrochlorination reaction section 142 in quenching section 152 wherein the effluent gas is directly contacted with a spray of quench liquid, in particular one or more of the chlorinated hydrocarbons produced in reaction section 141, introduced through line 153 to cool the effluent gas and thereby eliminate vaporized and entrained salts therefrom.

The effluent gas, now containing vaporized quench liquid, is withdrawn from vessel 133 through line 154 and introduced into a separation and recovery section (FIG. 3) for recovery of the various components.

A molten salt obtained from sections 141 and 142 is withdrawn from the bottom of reactor 133 through line 161 and lifted by lift gas in line 126 into a separation vessel 162 positioned adjacent the top of reactor 111. In separator 162, the molten salt is separated from the lift gas and introduced through line 110 into vessel 111. The lift gas is withdrawn from separator 162 through line 164 and combined with the lift gas in line 135 for introduction into the top quenching section of vessel 111 through line 113.

Referring now to FIG. 3, the reaction effluent in line 154 from reaction vessel 133 is cooled in condenser 310, primarily to condense a portion of the water therefrom (the condensed water would also contain hydrogen chloride, if present) the aforesaid cooling also resulting in the condensation of chlorinated hydrocarbons, including the chlorinated hydrocarbons used as quench liquid. The condensed water and chlorinated hydrocarbons are separated in a separator 311, with a water phase being withdrawn through line 312 and a chlorinated hydrocarbon phase being withdrawn through line 313. A portion of the chlorinated hydrocarbons in line 313 is recycled through line 153 as quench liquid for reactor 133. Alternatively, all of such chlorinated hydrocarbons, if required, may be recycled as quench liquid. The water phase in line 312 is stripped of entrained and dissolved chlorinated hydrocarbon in a stripping column (not shown) and the recovered chlorinated hydrocarbons (from the stripping column) in line 312a are combined with the chlorinated hydrocarbons in line 313. Depending on the amount of hydrogen chloride present in the water, the water may also be treated to recover hydrogen chloride or a concentrated solution of hydrogen chloride.

The remaining portion of the gaseous effluent in line 314 is optionally passed through an alkali scrubbing zone, of a type known in the art, schematically indicated as 315, to remove any remaining hydrogen chloride therefrom.

The gaseous effluent from the alkali scrubbing zone 315, if used, in line 316 is generally passed through a further cooling and separation zone, schematically indicated as 317, to condense further water and chlorinated hydrocarbons therefrom; an acid gas removal zone 318, of a type known in the art, to remove any acid gas, primarily carbon dioxide, and a drier 319, and introduced into a fractional distillation column 321. The chlorinated hydrocarbons in line 313 and chlorinated hydrocarbons separated in zone 317 are combined and dried in drier 320 for introduction into column 321. Alternatively, if required, a portion of the chlorinated hydrocarbons recovered in zone 317 may be recycled as quench liquid for reactor 133. The water separated in zone 317 may be passed to a stripping column to recover any chlorinated hydrocarbons with such recovered chlorinated hydrocarbons also being introduced into column 321.

The fractional distillation column 321 is operated at temperatures and pressures to produce a gaseous overhead comprised of ethane and ethylene, generally an overhead temperature from about 15° F to about −15° F, a bottom temperature from about 115° F to about 230° F and a pressure from about 2 atm to about 10 atm (absolute). The column 321 is provided with suitable reboil and reflux sections to provide the heat requirements for the column. A gaseous net overhead comprised of ethane and ethylene is recovered from column 321 in line 331 for use in the 1,1- 1,2-dichloroethane fractionator, as hereinafter described.

The bottoms from column 321, containing primarily vinyl chloride, ethyl chloride and 1,1- and 1,2-dichloroethane in line 322 is introduced into fractional distillation column 323 operated at temperatures and pressures to recover vinyl chloride as overhead, generally an overhead temperature from about 100° F to about 140° F, a bottoms temperature from about 210° F to about 255° F and a column pressure from about 6 atm to about 10 atm (absolute). The column 323 is provided with suitable reboil and reflux sections to meet the heat requirements of the fractionator. A net vinyl chloride product is recovered from column 323 in line 324.

The bottoms from column 323 containing ethyl chloride and 1,1- and 1,2-dichloroethane in line 325 is introduced into a fractional distillation column 326 operated at temperatures and pressures to recover 1,1-dichloroethane and lighter components as overhead, 1,2-dichloroethane as a bottoms vapor sidestream and components heavier than 1,2-dichloroethane as liquid bottoms, i.e., the conditions hereinabove described. A liquid bottoms comprised essentially of 1,2-dichloroethane and including a chlorination catalyst functions as the reaction medium for chlorinating the ethylene by-product introduced through line 331. The ethane-ethylene overhead in line 331 and fresh feed chlorine in line 332 are introduced into the bottom of column 326 to provide for the exothermic chlorination of ethylene to 1,2-dichloroethane. The column 326 is provided with reflux and reboil sections to meet the heat requirements for the column, but as a result of the exothermic chlorination of ethylene in column 326, the heat requirements for the reboil section are materially reduced or eliminated. The column 326, as shown, is designed and operated to recover 1,2-dichloroethane as a vapor sidestream in line 333 at the bottom of column 326, but it is to be understood that the 1,2-dichloroethane could also be recovered as liquid bottoms. The 1,2-dichloroethane also generally contains small amounts of heavier chlorinated hydrocarbons, such as one or more of the following: trichloroethane, trichloroethylene, tetrachloroethylene and tetrachloroethane, with the remainder of such heavier chlorinated hydrocarbons being recovered as bottoms in line 334. The heavier chlorinated bottoms may be burned and the combustion effluent recycled to vessel 111 through line 112a as hereinabove described.

The net vapor overhead from column 326 comprised primarily of 1,1-dichloroethane, ethane and ethyl chloride, and perhaps some ethylene, in line 145 is recycled to chlorination reactor 133.

The 1,2-dichloroethane recovered from column 326 in line 333 is passed to line 151 for introduction into the dehydrochlorination reaction section 142 of vessel 133.

It should be readily apparent that in accordance with the present invention 1,1-dichloroethane and 1,2-dichloroethane are effectively fractionated with reduced heat requirements, by effective utilization of components employed in the overall process for producing vinyl chloride.

It should be apparent that numerous modifications and variations of the hereinabove described embodiment are possible within the spirit and scope of the invention.

Thus, for example, although the process for separating 1,1- and 1,2-dichloroethane has been particularly described with reference to the production of vinyl chloride by the use of molten salts for both chlorination and dehydrochlorination, the process of the invention is equally applicable to a process in which chlorination is effected by molten salts and dehydrochlorination of 1,2-dichloroethane is effected in a conventional furnace. In such an embodiment, reactor 133 would not be divided into two zones, and 1,2-dichloroethane produced during the chlorination is dehydrochlorinated in a separate furnace. Such an embodiment can be more fully understood by reference to FIG. 4 of the drawings which illustrates the recovery and dehydrochlorination portion of such an embodiment, with the parts being designated by like prime numerals. The chlorination effluent in line 154' of the separation and recovery section is obtained by chlorination of ethane using a molten salt, as described with reference to FIG. 2. The operation of the initial portion of the separation and recovery section, including fractionators 321', 323' and 326' is as described with reference to the embodiment of FIG. 3 and, accordingly, no further description thereof is deemed necessary for an understanding of an embodiment which includes chlorination by molten salts and dehydrochlorination by conventional techniques.

1,2-dichloroethane withdrawn from fractionator 326' in line 333' is introduced into a dehydrochlorination furnace 401, of a type known in the art, operated at dehydrochlorination conditions to dehydrochlorinate the 1,2-dichloroethane to vinyl chloride and hydrogen chloride.

A dehydrochlorination effluent, which includes vinyl chloride, hydrogen chloride and unconverted 1,2-dichloroethane is withdrawn from furnace 401 in line 402 and introduced into a fractional distillation column 403 operated under conditions to recover hydrogen chloride, as an overhead product. The column 403 is provided with suitable reboil and reflux sections.

A hydrogen chloride overhead is recovered from column 403 in line 404 and recycled to the molten salt chlorination reactor (not shown) used in the reactor section.

The bottoms from column 403 in line 405 is introduced into a fractional distillation column 406 operated at conditions to recover vinyl chloride as an overhead product. The column 406 is provided with suitable reboil and reflux sections. Net vinyl chloride overhead product is recovered through line 407.

Bottoms from column 406 in line 408, comprised primarily of 1,2-dichloroethane is divided into a first portion which is passed through line 409 to the reflux section of column 403, and a second portion which is passed through line 411 and introduced into fractionator 326'.

As a further modification, it is also to be understood that 1,2-dichloroethane could be dehydrochlorinated by the use of molten salts in a reactor which is completely separate from the chlorination reactor. Similarly, the reaction effluents from the dehydrochlorination and chlorination need not be combined into a single stream as described with reference to the embodiment of FIG. 2.

The above modification and others should be apparent to those skilled in the art from the teachings herein.

The process of the present inventon is particularly advantageous in that 1,1-dichloroethane and 1,2-dichloroethane may be separated from each other with reduced utilities requirements.

The teachings of the present invention are particularly advantageous in the production of vinyl chloride from ethane by the use of molten salts, as described in aforementioned application Ser. Nos. 153,374 and 157,496 in that ethylene which is to be chlorinated is available as a by-product. Thus, in the absence of the present invention, ethylene is recycled to the chlorination zone, and by utilizing the teachings of the present invention, both the heat requirements for the fractionation and the vapor load to the chlorinator are reduced.

Numerous modification and variations of the present invention are possible and, therefore, within the scope of the appended claims the invention may be practiced in a manner other than as particularly described.

What is claimed is:

1. A process for separating 1,1-dichloroethane and 1,2-dichloroethane from a feed comprising a mixture thereof, comprising:

introducing said feed into a fractionation zone operated at temperatures and pressures to separate 1,1-dichloroethane, as overhead, from 1,2-dichloroethane; said fractionation zone being operated at an overhead temperature from about 170° F to about 310° F, a bottoms temperature from about 350° F to about 360° F and a column pressure from about 2 atm to about 10 atm (absolute); providing at least a portion of the heat requirements for the separation by introducing and reacting in the fractionation zone ethylene and chlorine to produce 1,2-dichloroethane; recovering separated 1,1-dichloroethane in a first stream as overhead withdrawn from said fractionation zone; and recovering separated 1,2-dichloroethane introduced as feed and produced from the chlorination of ethylene in a second stream withdrawn from said fractionation zone.

2. The process of claim 1 wherein the ethylene and chlorine are reacted in the fractionation zone in liquid 1,2-dichloroethane.

3. The process of claim 1 wherein said feed further includes ethyl chloride, said ethyl chloride being recovered in said first stream.

4. The process of claim 3 wherein said ethylene introduced into the fractionation zone also includes ethane, said ethane being recovered in said first stream.

* * * * *